United States Patent [19]

Streicher et al.

[11] Patent Number: 4,910,345
[45] Date of Patent: Mar. 20, 1990

[54] PROCESS FOR THE PURIFICATION OF NITROBENZALDENHYDE

[75] Inventors: Willi Streicher, Cologne; Heinz U. Blank, Odenthal-Gloebusch, both of Fed. Rep. of Germany

[73] Assignee: Bayer Aktiengesellschaft, Leverkusen, Fed. Rep. of Germany

[21] Appl. No.: 231,740

[22] Filed: Aug. 12, 1988

[30] Foreign Application Priority Data

Aug. 29, 1987 [DE] Fed. Rep. of Germany ....... 3728926

[51] Int. Cl.$^4$ ............................................. C07C 79/36
[52] U.S. Cl. .................................................. 568/424
[58] Field of Search ........................................ 568/424

[56] References Cited
PUBLICATIONS

Sugihara et al., J. Org. Chem. "Recrystallization of Organic Compounds from Detergent-Water Systems" pp. 1445–1447, 1956.

Hawley, Gessner, "The Condensed Chemical Dictionary" 1983 10th ed. pp. 314–315, 408–409, 929–930 and 986, Chem. Abs., vol. 101, 132169a, 1984, Mou, Yujain.

Primary Examiner—Donald B. Moyer
Assistant Examiner—Karen E. Plue
Attorney, Agent, or Firm—Sprung Horn Kramer & Woods

[57] ABSTRACT

Crude nitrobenzaldehyde can be substantially purified from the undesired positional isomers if a treatment with 100–10,000% by weight of water and 1–30% by weight of an emulsifier, all with reference to the dry weight of the crude nitrobenzaldehyde, is undertaken at a temperature of 30°–140° C. and at a pH of 3–14.

19 Claims, No Drawings

PROCESS FOR THE PURIFICATION OF NITROBENZALDENHYDE

BACKGROUND OF THE INVENTION

1. Field of the Invention

The invention relates to a process for the purification of crude nitrobenzaldehyde containing undesired positional isomers by treatment with water in the presence of an emulsifier.

2. Description of the Related Art

It is known from Houben-Weyl, Methoden der organischen Chemie (Methods of Organic Chemistry), Volume X/1, page 600 (1971) that a mixture of three possible isomers results from the nitration of benzaldehyde.

For the purification of the desired nitrobenzaldehyde, a recrystallization from organic solvents can be undertaken. By this means, serious losses of the desired product and considerable solvent costs results. When working on a commercial scale, additional precautions are necessary with regard to operational safety, recovery of the solvent, and health and environmental protection.

The recrystallization of organic materials from water in the presence of detergents is discussed in J. Org. Chem. 21 (1956), pp. 1445-1447. It was observed that the crystallization rate in the presence of surface-active agents is strongly lowered with organic compounds having limited water solubility. The procedure necessary is troublesome and characterized in that the organic substance only goes into solution slowly even on heating to boiling point, and in that a complete solution must be present, however, which is achieved, if appropriate, by hot filtration of undissolved constituents. Should the crystallization begin in the hot filtrate, it is heated once more to complete dissolution and slowly cooled. Data concerning the type and amount of the original impurities and data about the degree of purity obtained are not given.

SUMMARY OF THE INVENTION

It has now surprisingly been found that for the purification of crude nitrobenzaldehyde from its undesired positional isomers, it is not necessary to bring the starting material completely into solution and that accordingly no recrystallization is necessary. It is sufficient just to work in a two-phase system having a content of undissolved nitrobenzaldehyde. This procedure gives considerable advantages, among others in the space-time yield. The purification effect is considerable and is very surprising for a two-phase system having unpredictable surface reactions of the undissolved phase.

The invention thus relates to a process for the purification of crude nitrobenzaldehyde which is contaminated with its positional isomers, which is characterized in that the crude nitrobenzaldehyde is treated with 100-10,000% by weight of water and 1-30% by weight of emulsifier, all with reference to the dry weight of the crude nitrobenzaldehyde, at a temperature of 20°-140° C. and a pH of 3-14.

DETAILED DESCRIPTION OF THE INVENTION

The process according to the invention is carried out continuously or batchwise at a temperature of 20°-140° C., preferably 40°-120° C., without pressure or under pressure. 100-10,000% by weight, preferably 150-3,000% by weight, particularly preferably 150-800% by weight, of water and 1-30% by weight, preferably 2-20% by weight, of emulsifier, all with reference to the dry weight of the crude nitrobenzaldehyde, are used. A pH range of 3-14, preferably 5-13, is set according to the invention.

Emulsifiers for the process according to the invention are, for example, of the type that are described in Ullmanns Enzyklopädie der Technischen Chemie (Ullmann's Encyclopedia of Technical Chemistry), 4th edition, Volume 10 (1975), pp. 455 to 464. Cationic emulsifiers, anionic emulsifiers and non-ionic emulsifiers are included here. Cationic emulsifiers are, for example, primary, secondary or tertiary fatty amine salts, salts of alkylenediamines and of polyamines, quaternary alkylammonium salts, alkylbenzylammonium salts, quaternary amidoamine compounds, alkanolamine salts of ethers and esters, alkylpyridinium salts, and others. Anionic emulsifiers are, for example, carboxylates, such as soaps, salts of fluorinated carboxylic acids, alkoxycarboxylates, sulpho-soaps and sulphonamidocarboxylic acids; sulphonates, such as fatty acid sulphonates, fatty acid ester sulphonates, salts of sulphosuccinates, perfluorinated alkylsulphonates and alkylbenzenesulphonates; sulphates, such as sulphated soaps, esters, fatty acid amides, primary and secondary alcohols and alkanolamides; phosphoric acid compounds such as phosphates of alcohols, phenols or their polyglycol ethers, phosphates of glycols and glycerides, and esters of the phosphoric acids among others. Non-ionic emulsifiers are, for example, fatty acid esters of alcohols, ethylene glycol, polyethylene glycol, propylene glycol, glycerol; fatty amines and fatty acid amides, including fatty acid alkanolamides and polyamines, polyglycol ethers of alcohols, thioalcohols, fatty acids, fatty acid esters, fatty acid amines, fatty acid alkanolamides, fats and oils, polypropylene glycol, condensed phenols and condensed amines among others, and also the corresponding polypropylene glycol ethers of the compound classes mentioned.

The process according to the invention is equally utilizable on crude o-, m- or p-nitrobenzaldehyde. The crude nitrobenzaldehydes contain as impurities 0.1-15% by weight, preferably 0.1-10% by weight, particularly preferably 0.1-8% by weight, of the positional isomers in each case, with respect to the dry weight of the crude nitrobenzaldehyde. m- and p-Nitrobenzaldehyde are considered as undesired positional isomers, for example, in o-nitrobenzaldehyde. Either only one of the undesired positional isomers can be present or both can be present. The latter case is likely to be the rule.

Water-moist crude benzaldehyde can, of course, also be employed in the process according to the invention. The water content of the dry or water-moist crude nitrobenzaldehyde is 0-1,000% by weight, for example 0.1-1,000% by weight, preferably 1-800% by weight, particularly preferably 5-600% by weight, of water, with reference to the dry weight of the crude nitrobenzaldehyde. Water contents of this type are counted in the amount of water necessary for the process according to the invention. Low amounts of acids, for example from the nitration stage of the crude nitrobenzaldehyde, or of alkali, for example as the excess from a neutralization of acids of this type, and also of salts, for example from a neutralization of this type, are harmless for the process according to the invention. Should the pH lie outside the region according to the invention through this, it is brought into the region according to the invention by at least partial neutralization.

The crude nitrobenzaldehyde can, of course, also be employed in the form of acetals, which are expediently hydrolyzed to start with.

The process according to the invention can be carried out, for example, as follows: the necessary amounts of water and emulsifier, in which, for example, introduced water is counted, are added to the crude nitrobenzaldehyde. However, the emulsifier can also be added first and then the water. Furthermore, it is also possible to meter the nitrobenzaldehyde, the water and the emulsifier simultaneously. The metering of the components mentioned takes place, for example, at 10°-140° C., preferably at 15°-120° C. The desired reaction temperature and the desired pH are set. After cooling, the purified nitrobenzaldehyde present as the solid phase is separated in a customary manner, for example by filtration, from the aqueous phase, washed, or freshly filtered after fresh suspension in water, and finally dried.

The positional isomers contained in the crude nitrobenzaldehyde as impurities decline in their amount to 80% of their original value, in many cases to 60% or even less. With high impurities, an amount of emulsifier in the upper part of the region described above is in general employed; however, less emulsifier can also be employed in the case of lower purity requirements.

Nitrobenzaldehydes are well known to those skilled in the art as valuable starting materials, for example, for the preparation of dyes.

EXAMPLES

Example 1

190.0 g of water-moist m-nitrobenzaldehyde (containing 163.0 g of crude nitrobenzaldehyde of the composition: 1.5% by weight of o-isomer; 2.3% by weight of p-isomer; 96.2% by weight of m-isomer) were suspended in 445 g of water and 20.0 g of an emulsifier, which was prepared by condensation of m-cresol, formaldehyde, sodium sulphite and 2-naphthol-6-sulphonic acid, were added. The suspension was heated to 60° C. and adjusted to pH 10.4 using NaOH. The mixture was subsequently heated to reflux and stirred under reflux for 30 minutes. It was then cooled to 40° C., stirred at 40° C. for 2.5 hours and filtered off with suction. The filtered material was washed with water and freshly filtered with suction. After drying, 141.7 g of m-nitrobenzaldehyde were obtained.

Content in % by weight 0.06 o-nitrobenzaldehyde
99.8 m-nitrobenzaldehyde
0.1 p-nitrobenzaldehyde The remainder to 100% consists of components which were not investigated more closely (this also supplies to the further example).

Yield: 93.1% (with reference to m-nitrobenzaldehyde employed)

Example 2

190.0 g of water-moist m-nitrobenzaldehyde of composition as in Example 1 were suspended in 445.0 g of water and 10.0 g of the emulsifier used in Example 1 were added and the mixture was purified according to the procedure described in Example 1.

After drying, 144.6 g of m-nitrobenzaldehyde were obtained.

Content in % by weight 0.08 o-nitrobenzaldehyde
99.7 m-nitrobenzaldehyde
0.2 p-nitrobenzaldehyde Yield: 95% (with reference to m-nitrobenzaldehyde employed)

Example 3 (for comparison)

190.0 g of water-moist m-nitrobenzaldehyde of composition as in Example 1 were suspended in 445.0 g of water and purified without emulsifier according to the procedure described in Example 1.

After drying, 147.4 g of m-nitrobenzaldehyde were obtained.

Content in % by weight 0.8 o-nitrobenzaldehyde
97.6 m-nitrobenzaldehyde
1.6 p-nitrobenzaldehyde Yield: 95.3% (with reference to m-nitrobenzaldhyde employed)

Example 4

63.4 g of water and 1.63 g of monohydrate (100% strength $H_2SO_4$) were metered into 211.0 g of m-nitrobenzaldehyde dimethylacetal of composition: 1.6% by weight of o-isomer; 2.4% by weight of p-isomer; 95.6% by weight of m-isomer; and 0.4% by weight of various impurities. The mixture was then heated with stirring and the methanol/water mixture resulting from the acetal cleavage was removed by distillation at a bottom temperature of 80°-106° C. via a simple distillation apparatus.

After the distillation, 445.0 g of water were added to the distillation residue; the mixture was neutralized using sodium hydroxide solution and 10.0 g of the emulsifier used in Example 1 were metered in; the mixture was then stirred under reflux for 30 minutes. The emulsion was cooled to 40° C. with stirring and stirred at 40° C. for 2.5 hours. The precipitated m-nitrobenzaldehyde was filtered off with suction, washed with water and freshly filtered off with suction.

After drying, 144.3 g of m-nitrobenzaldehyde were obtained.

Content in % by weight 0.05 o-nitrobenzaldehyde
99.6 m-nitrobenzaldehyde
0.3 p-nitrobenzaldehyde Yield: 92.5% (with reference to m-nitrobenzaldehyde employed)

Example 5

63.4 g of water and 1.63 g of monohydrate (100% strength $H_2SO_4$) were metered into 211.0 g of m-nitrobenzaldehyde dimethylacetal of composition as in Example 4. The mixture was then heated with stirring and the methanol/water mixture resulting from the acetal cleavage was removed by distillation at a bottom temperature of 80°-106° C. via a simple distillation apparatus. After the distillation, 445.0 g of water were added to the distillation residue; the mixture was neutralized using sodium hydroxide solution and 10.0 g of di-sec.-butyl-naphthalene-sulphonic acid sodium salt were added. The mixture was then further processed as in Example 4.

After drying, 145.7 g of m-nitrobenzaldehyde were obtained.

Content in % by weight 0.2 o-nitrobenzaldehyde
98.9 m-nitrobenzaldehyde
0.4 p-nitrobenzaldehyde
Yield: 93.2% (with reference to m-nitrobenzaldehyde employed)

Example 6

211.0 g of m-nitrobenzaldehyde dimethylacetal of composition as in Example 4 were reacted according to Example 4. 10.0 g of benzyl-dodecyl-dimethyl-ammonium chloride were used as the emulsifier.

After drying, 145.2 g of m-nitrobenzaldehyde were obtained.

Content in % by weight 0.1 o-nitrobenzaldehyde
99.1 m-nitrobenzaldehyde
0.7 p-nitrobenzaldehyde
Yield: 93.1% (with reference to m-nitrobenzaldehyde employed)

Example 7

63.4 g of water and 1.63 g of monohydrate (100% strength $H_2SO_4$) were metered into 211.0 g of m-nitrobenzaldehyde dimethylacetal of composition: 1.3% by weight of o-isomer; 5.6% by weight p-isomer; 92.7% by weight of m-isomer; 0.4% by weight of various impurities. The mixture was then heated under reflux and the methanol/water mixture resulting from the acetal cleavage was removed by distillation at a bottom temperature of 80°–106° C. via a simple distillation apparatus. After the distillation, 445.0 g of water were added to the distillation residue; the mixture was neutralized using sodium hydroxide solution, and 20.0 g of the emulsifier used in Example 1 were metered in. The emulsion was stirred for 30 minutes at reflux, cooled to 40° C. with stirring and stirred at 40° C. for 2.5 hours. The precipitated m-nitrobenzaldehyde was filtered off with suction, washed with water and freshly filtered with suction.

After drying, 133.7 g of m-nitrobenzaldehyde were obtained.

Content in % by weight 99.4 m-nitrobenzaldehyde
0.4 p-nitrobenzaldehyde
remainder other impurities
Yield: 88.6% (with reference to m-nitrobenzaldehyde employed)

Examples 8–10

75.5 g of 90% pure m-nitrobenzaldehyde containing 5% of o-isomer and 5% of p-isomer and the emulsifier mentioned in Example 1 were in each case employed according to the fundamental procedure of Example 1. Table 1 gives the amounts of water and emulsifier, the composition of the product and the yield in % of the theoretical yield.

TABLE 1

| | Purification of m-nitrobenzaldehyde | | | | | | |
|---|---|---|---|---|---|---|---|
| | $H_2O$ | Emulsifier | | Product (% by weight) | | | Yield |
| Example | (% by weight) | (g) | (% by weight) | o- | m- | p- | (%) |
| 8 | 200 | 15.1 | 20 | 1.5 | 97.0 | 1.5 | 82.0 |
| 9 | 700 | 15.1 | 20 | 1.3 | 97.5 | 1.2 | 82.0 |
| 10 | 700 | 2.3 | 3 | 2.2 | 94.8 | 3.0 | 90.0 |

Examples 11–21

In the same manner as in Examples 8–10, 75.5 g of o-nitrobenzaldehyde of the given composition and the emulsifier mentioned in Example 1 were in each case employed. Table 2 contains all additional data.

Examples 22–25

In the same manner as in the Examples 8–10, 75.5 g of p-nitrobenzaldehyde of the given composition and the emulsifier mentioned in Example 1 were in each case employed. Table 3 contains all additional data.

TABLE 2

| | Purification of o-nitrobenzaldehyde | | | | | | | | | |
|---|---|---|---|---|---|---|---|---|---|---|
| | Start (% by weight) | | | $H_2O$ | Emulsifier | | Product (% by weight) | | | Yield |
| Example | o- | m- | p- | (% by weight) | (g) | (% by weight) | o- | m- | p- | (%) |
| 11 | 96 | 3 | 1 | 273 | 5.0 | 6.3 | 99.1 | 0.8 | 0.1 | 95 |
| 12 | 96 | 3 | 1 | 273 | 10.0 | 12.6 | 99.7 | 0.3 | — | 92 |
| 13 | 90 | 5 | 5 | 200 | 15.1 | 20.0 | 95.5 | 2.2 | 2.3 | 87 |
| 14 | 90 | 5 | 5 | 700 | 15.1 | 20.0 | 95.9 | 1.4 | 2.7 | 87 |
| 15 | 90 | 5 | 5 | 700 | 2.3 | 3.0 | 92.5 | 3.7 | 3.8 | 95.3 |
| 16 | 90 | 5 | 5 | 700 | 30.2 | 40.0 | 98.5 | 0.8 | 0.7 | 80.4 |
| 17 | 96 | 3 | 1 | 273 | — | —* | 96.2 | 2.9 | 0.9 | 98 |
| 18 | 96 | 3 | 1 | 273 | 5.0 | 6.3** | 98.6 | 1.2 | 0.2 | 97.5 |
| 19 | 96 | 3 | 1 | 273 | 5.0 | 6.3*** | 98.4 | 1.3 | 0.3 | 97 |
| 20 | 95 | 2.5 | 2.5 | 700 | 10.0 | 12.6 | 98.7 | 0.7 | 0.6 | 91 |
| 21 | 95 | 2.5 | 2.5 | 700 | 15.1 | 20.0 | 99.4 | 0.4 | 0.2 | 89.5 |

*without emulsifier; comparison experiment
**Zephirol emulsifier: benzyl-dodecyl-dimethyl-ammonium chloride
***Erkantol BXG emulsifier: di-sec.-butyl-naphthalene-sulphonic acid sodium salt

TABLE 3

| | Purification of p-nitrobenzaldehyde | | | | | | | | | |
|---|---|---|---|---|---|---|---|---|---|---|
| | Start (% by weight) | | | $H_2O$ | Emulsifier | | Product (% by weight) | | | Yield |
| Example | o- | m- | p- | (% by weight) | (g) | (% by weight) | o- | m- | p- | (%) |
| 22 | 5 | 5 | 90 | 700 | 5.0 | 6.3 | 1.3 | 2.0 | 96.7 | 96 |
| 23 | 5 | 5 | 90 | 700 | 15.1 | 20 | 0.6 | 1.0 | 98.4 | 95 |

TABLE 3-continued

Purification of p-nitrobenzaldehyde

| Ex-ample | Start (% by weight) | | | H₂O (% by weight) | Emulsifier | | Product (% by weight) | | | Yield (%) |
|---|---|---|---|---|---|---|---|---|---|---|
| | o- | m- | p- | | (g) | (% by weight) | o- | m- | p- | |
| 24 | 5 | 5 | 90 | 700 | 22.7 | 30 | 0.3 | 1.3 | 98.4 | 92.7 |
| 25 | 2.5 | 2.5 | 95 | 700 | 15.1 | 20 | — | 0.3 | 99.7 | 95 |

What is claimed is:

1. A process for the purification of o-, m- or p-nitrobenzaldehyde which is contaminated by one or both of its remaining undesired positional isomers, comprising suspending the o-, m- or p-nitrobenzaldehyde which is contaminated by one or both of its undesired remaining position isomers, in 100–10,000% by weight of water and 1–30% by weight of emulsifier at a temperature of 20° C. to 140° C. and a pH of 3–14, all with reference to the dry weight of the nitrobenzaldehyde, without recrystallization, to form a two-phase system and separating out the purified nitrobenzaldehyde.

2. A process according to claim 1, wherein the nitrobenzaldehyde contains 0.1–15% by weight of undesired positional isomers.

3. A process according to claim 2, wherein the nitrobenzaldehyde contains 0.1–10% by weight of undesired positional isomers.

4. A process according to claim 3, wherein the nitrobenzaldehyde contains 0.1 to 8% by weight of undesired positional isomers.

5. A process according to claim 1, wherein the nitrobenzaldehyde is employed in a dry form or the nitrobenzaldehyde has a water content.

6. A process according to claim 5, wherein the water content of the nitrobenzaldehyde is 0.1 to 1,000% by weight, with reference to the weight of dry nitrobenzaldehyde.

7. A process according to claim 6, wherein the water content is 1–800% by weight.

8. A process according to claim 7, wherein the water content is 5–600% by weight.

9. A process according to claim 1, wherein the weight % of water is 150–3000.

10. A process according to claim 1, wherein the pH is adjusted to 5–13 for the process.

11. A process according to claim 1, wherein a temperature of 40°–120° C. is used for the process.

12. A process according to claim 1, wherein the weight % of emulsifier is 2–20%.

13. A process according to claim 1, wherein said emulsifier is a cationic emulsifier, an anionic emulsifier or a non-ionic emulsifier.

14. A process accoridng to claim 13, wherein said cationic emulsifier is a primary fatty amine salt, a secondary fatty amine salt, a tertiary fatty amine salt, a salt of an alkylenediamine, a salt of a polyamine, a quaternary alkylammonium salt, an alkylbenzylammonium salt, a quaternary amidoamine compound, an alkanolamine salt of an ether, an alkanolamine salt of an ester or an alkylpyridinium salt.

15. A process according to claim 13, wherein said anionic emulsifier is a carboxylate, a sulphonate, a sulphate or a phosphoric acid compound.

16. A process according to claim 13, wherein said anionic emulsifier is a soap.

17. A process according to claim 13, wherein said anionic emulsifier is a salt of a fluorinated carboxylic acid, an alkoxy carboxylate, a sulpho-soap, a sulphonamidocarboxylic acid, a fatty acid sulphonate, a fatty acid ester sulfonate, a salt of a sulphosuccinate, a perfluorinated alkyl sulphonate, an alkylbenzenesulphonate, a sulphated soap, ester, fatty acid amide, primary alcohol, secondary alcohol or alkanolamide, a phosphate of an alcohol, a phosphate of a phenol, a phosphate of a glycol, a phosphate of a glyceride or an ester of a phosphoric acid.

18. A process according to claim 13, wherein the non-ionic emulsifier is a fatty acid ester of an alcohol, ethylene glycol, polyethylene glycol, propylene glycol or glycerol, a fatty amine or a fatty acid amide.

19. A process according to claim 13, wherein the non-ionic emulsifier is a fatty acid alkanolamide or polyamine, a polyglycol ether of an alcohol, thioalcohol, fatty acid, fatty acid ester, fatty acid amine, fatty acid alkanolamide, fat, oil, polypropylene glycol, condensed phenol or condensed amine.

* * * * *